(12) United States Patent
Mora-Gutierrez et al.

(10) Patent No.: US 7,118,688 B2
(45) Date of Patent: Oct. 10, 2006

(54) ANTIOXIDANT COMPOSITIONS AND METHODS OF USE THEREOF

(75) Inventors: Adela Mora-Gutierrez, Houston, TX (US); Michael H. Gurin, Glenview, IL (US)

(73) Assignee: The Texas A&M University System, College Station, TX (US)

(*) Notice: Subject to any disclaimer, the term of this patent is extended or adjusted under 35 U.S.C. 154(b) by 0 days.

(21) Appl. No.: 10/784,842

(22) Filed: Feb. 23, 2004

(65) Prior Publication Data

US 2005/0184275 A1    Aug. 25, 2005

(51) Int. Cl.
    C09K 15/32    (2006.01)
    C09K 15/22    (2006.01)
    C09K 15/20    (2006.01)
    A23J 7/00     (2006.01)
    C07F 9/02     (2006.01)

(52) U.S. Cl. ............ 252/400.21; 252/400.22; 252/401; 252/402; 426/662; 426/602; 426/604; 426/631; 435/68.1; 435/272

(58) Field of Classification Search ........ 252/400.21, 252/400.22, 401, 402; 426/546, 544, 602, 426/604, 654, 656, 662, 658, 631
See application file for complete search history.

(56) References Cited

U.S. PATENT DOCUMENTS

| | | | | |
|---|---|---|---|---|
| 2,282,790 A | * | 5/1942 | Musher | 554/2 |
| 2,282,812 A | * | 5/1942 | Musher | 554/2 |
| 2,282,815 A | * | 5/1942 | Musher | 554/4 |
| 3,887,715 A | * | 6/1975 | Cante et al. | 426/570 |
| 3,957,837 A | * | 5/1976 | Sims et al. | 554/6 |
| 4,284,630 A | * | 8/1981 | Yu et al. | 514/179 |
| 4,421,778 A | * | 12/1983 | Kahn et al. | 426/564 |
| 4,716,036 A | * | 12/1987 | Schelm | 424/57 |
| 4,915,876 A | * | 4/1990 | Lindsay | 554/3 |
| 4,963,385 A | * | 10/1990 | Antrim et al. | 426/602 |
| 5,015,628 A | * | 5/1991 | Reynolds | 514/12 |
| 5,077,069 A | * | 12/1991 | Chang et al. | 426/330.6 |
| 5,102,659 A | * | 4/1992 | Hudson | 424/745 |
| 5,116,629 A | * | 5/1992 | Schroeder et al. | 426/545 |
| 5,139,796 A | * | 8/1992 | Barkalow et al. | 426/3 |
| 5,143,737 A | * | 9/1992 | Richardson | 426/2 |
| 5,223,285 A | * | 6/1993 | DeMichele et al. | 426/72 |
| 5,227,154 A | * | 7/1993 | Reynolds | 424/49 |
| 5,230,916 A | * | 7/1993 | Chang et al. | 426/330.6 |
| 5,258,179 A | * | 11/1993 | Bracco et al. | 424/94.1 |
| 5,290,685 A | * | 3/1994 | Koide et al. | 435/68.1 |
| 5,405,756 A | * | 4/1995 | Naito et al. | 435/68.1 |
| 5,427,814 A | * | 6/1995 | Loliger et al. | 426/610 |
| 5,486,376 A | * | 1/1996 | Alander et al. | 426/660 |
| 5,650,190 A | * | 7/1997 | Buikstra et al. | 426/602 |
| 5,705,187 A | * | 1/1998 | Unger | 424/450 |
| 5,834,427 A | * | 11/1998 | Han et al. | 514/12 |
| 5,981,475 A | * | 11/1999 | Reynolds | 514/6 |
| 6,140,375 A | * | 10/2000 | Nagahama et al. | 516/73 |
| 6,217,879 B1 | * | 4/2001 | Suetsuna et al. | 424/195.17 |
| 6,298,859 B1 | * | 10/2001 | Kierulff et al. | 131/297 |
| 6,630,188 B1 | * | 10/2003 | Breivik et al. | 426/321 |
| 6,656,511 B1 | * | 12/2003 | Kumagai | 424/757 |
| 2004/0091598 A1 | * | 5/2004 | Decker et al. | 426/602 |

OTHER PUBLICATIONS

PCT International Search Report for International Application No. PCT/US04/05401, 11 pages, Mailing Date Oct. 27, 2004.

* cited by examiner

*Primary Examiner*—Joseph D. Anthony
(74) *Attorney, Agent, or Firm*—David G. Rosenbaum; Rosenbaum & Associates, PC

(57) ABSTRACT

An antioxidant composition having enhanced oxidative stability, emulsion stability, and health benefits. The composition may include individual ingredients or a synergistic blend of non-reducing sugars, sugar polyols, medium-chain triglycerides, polysaccharides, polyphenols, phospholipids, chitosan, and alpha-casein, beta-casein, kappa-casein or protein fragments, glycopeptides, phosphopeptides. The composition may optionally be further utilized for the prevention of hypercholesterolemia or bone mineral loss.

35 Claims, No Drawings

ANTIOXIDANT COMPOSITIONS AND METHODS OF USE THEREOF

FIELD OF THE INVENTION

The present invention relates to antioxidant compositions, particularly compositions formed from natural ingredients, and methods for using said compositions to stabilize emulsions containing highly polyunsaturated lipids.

BACKGROUND

It is known that whatever their kind and origin, fats and oils have limited stability. During storage they undergo various deteriorative reactions that reduce their nutritive value and also produce volatile compounds, giving off unpleasant smells and tastes. In general, the term rancidity has been used to describe the mechanisms by which lipids alter in nature, mechanisms that may have a biological or chemical origin. Alterations of a biological nature include those produced by microorganisms (e.g., bacteria, fungi and yeasts) that may be inhibited by the addition of preservatives, and those produced by enzymes, mainly hydrolytic rancidity or lipolysis. The latter may be inhibited by thermal treatment, by conservation at low temperature, or by reducing the percentage of water.

Alterations of a chemical nature are due to the action of oxygen. Lipid oxidation reactions, known as autooxidation, commonly occur in lipids with a high content of unsaturated fatty acids and constitute the most common deterioration of fats and oils. However, unsaturated fatty acids are not the only constituents in foods that undergo oxidation. Compounds that impart color and taste to foods, like some vitamins, are also susceptible to oxidation.

It has been shown that the oxidation of unsaturated fatty acids takes place through a chain reaction that essentially consists of an initiation or induction stage, which implies the formation of fat free radicals; a propagation stage in which fat free radicals remove a hydrogen atom from a lipid to form a relatively stable hydroperoxide and a new unstable fat free radical. These hydroperoxides may interact with proteins, pigments, and other food constituents to generate substances whose chemical nature may be harmful to human health. As a final step in autooxidation, the hydroperoxides split into smaller short chain organic compounds such as aldehydes, ketones, alcohols, and acids which cause the off-odors and off-flavors characteristic of rancid fats and oils.

In plants, the most widespread polyunsaturated fatty acids are linoleic acid (Omega-6) and alpha-linolenic acid (Omega-3). Many vegetable oils contain Omega-6 fatty acid (linoleic acid). However, unlike many other vegetable oils, flaxseed oil also contains significant amounts (generally about 55 to about 65 percent) of Omega-3 fatty acid (alpha-linolenic acid). Their presence in food is of great importance since they cannot be synthesized by human and animal tissues and should thereby be provided with the diet. In tissues these essential fatty acids are converted to longer and more unsaturated fatty acids of the Omega-6 and Omega-3 families, such as arachidonic acid (AA), eicosapentaenoic (EPA), and docosahexaenoic (DHA), which are present in fish oil in relatively high amounts. The health benefits of linoleic acid, alpha-linolenic acid, AA, EPA and DHA are well documented in the literature. These benefits include hypolipidemic, anti-thrombotic, and anti-inflammatory properties. They are also essential fats for growth, brain function, and visual acuity, especially for infants. The degree of unsaturation of highly unsaturated fatty acids makes them extremely sensitive to oxidation, resulting in lipid peroxide and subsequent development of off flavors, odors, and dark color, which decrease the nutritive value of polyunsaturated oils and related food. The rate at which the oxidation reaction proceeds depends on several factors such as temperature, degree of unsaturation of the lipids, oxygen level, ultraviolet light exposure, presence of trace amounts of pro-oxidant metals (i.e., iron, copper, nickel), lipoxidase enzymes, and so forth. Flaxseed oil and fish oil can become rancid in few weeks or less, even if refrigerated.

The presence of certain chemical compounds may inhibit the process of lipid oxidation. The term "antioxidants" in foods is usually applied to those compounds that interrupt the chain reaction involved in autooxidation. Primary antioxidants are those mainly phenolic antioxidants, that interrupt the chain of free radicals and among which are found natural and synthetic antioxidants such as tocopherols, butylated hydroxyanisol (BHA), butylhydroxytoluene (BHT), tertiary butylated hydroquinone (TBQH), and propyl gallate. All of them act as donors of electrons.

It has been long recognized that various acids, and some of their derivatives, provide apparent antioxidant effect when added to vegetable oils. These are commonly referred to as acid-type antioxidants. However, these acids, if added alone to oils containing no primary antioxidant, will exhibit virtually no effect on the oxidative stabilities of the oil. It is believed that the acids are not truly antioxidants but more likely function by enhancing, in some manner, the activity of primary antioxidants naturally present (such as tocopherol) in the oils, or those synthetic antioxidants that are added. Common acid-type antioxidants include ascorbic acid, ascorbyl palmitate, and erithorbic acid. Unlike the primary antioxidants that function as electron donors, ascorbic acid and ascorbyl palmitate function by the entirely different mechanism of oxygen scavenging. Pro-oxidation occurs in lipid-based systems containing certain metal ions and reducing agents. Casein has been shown to act as a non-reducing agent by oxidizing iron from its ferrous to the ferric form (Emery T. in Biochem. Biophys. Res. Comm. 182, 1047–1052 (1992)). Polyphenol-rich extracts from a variety of plant sources e.g., tea, coffee, cocoa, wine, aloe vera, and oak leaves and bark are known to extend the shelf life of products by inhibiting oxidative rancidity.

Polyphenols inhibit free radical formation and the propagation of free radical reactions through the chelation of transition-metal ions, particularly those of iron and copper (Brown et al. in Biochem. J 330, 1173–1178 (1998)). Citric acid, amino acids, and ethylenediaminetetraacetic acid also form chelates with metallic ions such as copper and iron, thus avoiding their catalytic action on the oxidation of lipids. Most of these chelating agents exhibit little or no antioxidant activity when used alone, and therefore they are considered as synergistic agents of other antioxidants. Thus, they increase, to a great extent, the action of primary antioxidants.

Numerous extracts from plants and spices such as rosemary, sage, thyme, oregano, cloves, ginger, mace and nutmeg, exhibit antioxidant activity. However, these natural antioxidants are not very effective and suffer from the disadvantage of having intensive characteristic herb and spice flavors, which may limit their use in some applications. Many different natural antioxidant compositions have been developed over the years. Natural antioxidant compositions are typically blends of ascorbic acid (vitamin C), tocopherol (vitamin E), citric acid, rosemary extract, and phospholipids (i.e., soybean lecithin, egg yolk lecithin).

Ascorbyl palmitate is also used in these natural antioxidant compositions. For example, U.S. Pat. No. 5,077,069 discloses a complex of tocopherol, ascorbic acid, citric acid and phospholipids that are useful in preventing oxidation of oils. U.S. Pat. No. 5,102,659 discloses a complex of ascorbyl palmitate, a mixed tocopherol concentrate, and rosemary extract useful for prolonging the shelf life of vitamin/dietary supplements which are highly susceptible to rancidity. U.S. Pat. No. 5,230,916 discloses an ascorbic acid complex for stabilizing polyunsaturated oil. U.S. Pat. No. 5,258,179 discloses the use of coenzyme Q in combination with ascorbic acid and phospholipid to provide protection from oxidation. U.S. Pat. No. 5,427,814 describes the use of a mixture of tocopherol, lecithin, and ascorbic acid to protect lipids against oxidation.

These natural antioxidant compositions also suffer from problems that limit their usefulness. Thus, the combination of ascorbic acid and lecithin (an ionic phospholipid) is known to produce an undesirable red color in the oil. A high amount of lecithin may also impart an undesirable odor and flavor to the product. Ascorbic acid is ineffective as an antioxidant in hydrophobic substrates. Esters of ascorbic acid with saturated fatty acids particularly ascorbyl palmitate and ascorbyl stearate are used instead. However, these fat-soluble ester derivatives are exceptionally costly and do not fall within the narrow definition of natural. It is also costly to remove objectionable solvents used to dissolve oil-insoluble compounds present in these natural antioxidant compositions.

Many products susceptible to oxidation are emulsions or may be made into emulsions. An emulsion is a colloidal dispersion of two immiscible liquids, such as oil and water, in the form of droplets. If oil droplets are finely dispersed in water, then this is an oil-in-water or "O/W" emulsion. When water droplets are finely dispersed in oil, then this is a water-in-oil or "W/O" emulsion. O/W and W/O emulsions play a prominent role in the preparation of a wide range of products including foods, pharmaceutical products and cosmetics. It would be thus desirable to provide antioxidant compositions formed from natural ingredients and methods to effectively reduce oxidation reactions within highly polyunsaturated oils in O/W and W/O emulsions.

SUMMARY OF THE INVENTION

The present invention relates to compositions and methods for enhancing the inhibition of oxidation within highly polyunsaturated lipids in O/W and W/O emulsions. Particular embodiments of the present invention relate to a process for the protection against oxidation of O/W and W/O emulsions containing highly polyunsaturated lipids, characterized in that effective quantities of tocopherols, beta-carotene, egg yolk or soybean phospholipids, and sucrose or sorbitol are incorporated in the O/W and W/O emulsions by homogenization.

When used in the presence of caprine caseinophosphopeptide, eggplant (LBJ 10), and citric acid, certain embodiments of the present invention show enhanced antioxidant activity. In addition, antioxidant compositions may offer nutritional benefits including the formation of: (1) insoluble and unabsorbable calcium and magnesium chelates with fatty acids, having cholesterol-lowering activity in animal bodies; and (2) soluble complexes with calcium and magnesium, preventing bone mineral loss in animal bodies.

Specific embodiments of the present invention are further described in the following detailed description.

DETAILED DESCRIPTION

The present invention includes compositions and methods for enhancing inhibition of oxidation. The antioxidant compositions may inhibit oxidation of highly polyunsaturated lipids. They may include non-reducing sugars, sugar polyols, medium-chain triglycerides, sulfated polysaccharides, caseinophosphopeptides, phospholipids, chitosan and polyphenols. These antioxidant compositions may be used in O/W or W/O emulsions.

Selected embodiments contain sulfated polysaccharides. These may include compounds containing at least one polymeric sugar moiety covalently attached to a sulfate group. One example of a sulfated polysaccharide is the carrageenan class of compounds. Other examples of sulfated polysaccharides include chondroitin sulfate, sulfated cyclodextrins, dextran sulfate and heparin sulfate.

The antioxidant compositions may also include ingredients selected from the group of non-reducing sugars, sugar polyols, medium-chain triglycerides, polysaccharides, alpha-casein, beta-casein, kappa-casein or protein fragments, glycopeptides, phosphopeptides, alpha, beta, gamma or delta tocopherols, alpha, beta, gamma or delta tocotrienols, tocopherols, tocotrienols, beta-carotene, phospholipids and chitosan, or combinations thereof.

The antioxidant compositions may also include pH modifiers including citric acid, ascorbic acid, gluconic acid, and chelating agents including citric acid, or combinations thereof.

The antioxidant compositions may include polyphenols derived from the fruit of Solanum melongena.

In selected embodiments, the antioxidant compositions include a microemulsion or nanoemulsion with ingredients including: non-reducing sugars, sugar polyols, or combinations thereof; modified starches; polysaccharides; glycerides selected from enzymatically modified oils, fats, and fatty acids of mono-, di-, and tri-glycerides; glycerides selected from lipolyzed modified oils, fats, and fatty acids of mono-, di-, and tri-glycerides; fruit concentrate sweetener as humectant that comprises a blend of hydrolyzed starch having a dextrose equivalent (D.E.) of up to approximately 25; fruit juice or fruit syrup concentrate of at least approximately 40% soluble solids and approximately 0% insoluble solids thereby forming a liquor having a dry weight composition of approximately 40 to approximately 65% complex carbohydrates; and approximately 35 to approximately 55% simple sugars from the fruit juice or fruit syrup concentrate; and approximately 0 to approximately 5% nutritional components occurring naturally in the fruit juice or fruit syrup concentrate; cocoa powder; Sucralose; and combinations thereof.

In other embodiments, the antioxidant compositions may be made into products including: hypercholesterolemia prevention products in a mammal comprised of calcium and magnesium salts; bone mineral loss prevention products in a mammal comprised of calcium and magnesium salts; oils rich in Omega-3 products comprised of calcium and magnesium salts; oil-soluble flavor products; oil-soluble vitamin, nutraceutical, or pharmaceutical products; products having vegetable oils including rice bran oil, flax, chia, hemp, castor, soybean, lesquerella, dehydrated castor oil, rich in Omega-3, or conjugated linoleic acid, animal oils including fish, egg, poultry, and beef oils rich in Omega-3, or conjugated linoleic acid, or combinations thereof; beverage products being transparent comprised of calcium and magnesium salts; cocoa products having improved creaminess, reduced bitterness, and reduced oxidation; protein rich products, comprised of high-methoxyl pectins or pectin alginates or combinations thereof having reduced protein settling and sedimentation; protein rich products having reduced protein settling and sedimentation; oil-in-water micro- and nano-emulsions having increased emulsion and oxidation stability; or water-in-oil micro- and nano-emulsions having increased emulsion and oxidation stability.

The present invention may function as an antioxidant in a variety of ways. For instance, sucrose has demonstrated its potential as a fat-solubilizing agent for natural vitamins such as provitamin A (beta-carotene) and vitamin E (tocopherol) as well as polyphenolic compounds and caprine caseinophosphopeptide and as an antioxidant agent (invert sugar) in fat emulsions. Invert sugar is a mixture of about 50% glucose (dextrose) and 50% fructose (levulose) obtained by hydrolysis of sucrose. Hydrolysis of sucrose may be carried out with acids or enzymes. Honey is mostly invert sugar. The addition of 15% honey to ground turkey has shown to reduce the rate of oxidation compared to the 0 and 5% honey samples (Anthony et al. in J. Food Sci. 67, 1719–1724 (2002)). It has been theorized that the Maillard reaction products (MRPs) are the source of the antioxidative effect.

The nonenzymatic interaction between reducing sugars with amino acids, peptides, or proteins has been referred to as the Maillard browning reaction (MR). MR is known to produce a multitude of intermediates, which are collectively referred to as Maillard reaction products (MRPs). The formation of MRPs is greatly influenced by both the source of reactants and the reactant conditions, and even fixed reactant and reaction conditions are also known to produce a variety of MRPs. MRPs are derived by thermal decomposition of reducing sugar-amino acid compounds, and have been shown to possess both antioxidative and prooxidative activities (Wijewickreme A. N. and Kitts D. D. in J. Agric. Food Chem. 45, 4571–4576 (1997)).

The oxidative behavior of the MRPs formed by reacting sucrose with the caseinophosphopeptide-chitosan complex of the present invention, when evaluated in an O/W emulsion system containing $Fe^{2+}$ ions and determined by an oxygen electrode method, consisted of MRPs with low antioxidant activity at 3% sucrose concentration and prooxidant activity at 6% sucrose concentration. MRPs formed after heating the caseinophosphopeptide-chitosan complex of the present invention and sucrose for 2 h at 120 □C contribute to the decreased antioxidant activity. On the contrary, treatment of the caseinophosphopeptide-chitosan complex of the present invention with sorbitol inhibited MRP formation. Thus, sorbitol maintained the antioxidant activity of the caseinophospetide-chitosan complex of the present invention very effectively when added at the 3 and 6% level to an O/W emulsion system containing $Fe^{2+}$ ions.

The observation that browning, assessed visually, increased with increasing sucrose concentration at a fixed antioxidant composition concentration indicates that there was a greater extent of Maillard reaction and therefore, it is expected that the rate and extent of acid development were increased. It is known that acid is formed during the Maillard reaction (McGookin, B. J. and Augustin, M. A. in J. Dairy Res. 58, 313–320 (1991)). A more extensive acid hydrolysis of sucrose into glucose and fructose (invert sugar) reduces the ability of the caseinophosphopeptide-chitosan complex of the present invention to prevent oxidation. The formation of MRPs from both glucose-caseinophosphopeptide/chitosan and fructose-caseinophosphopeptide/chitosan reactions impairs the antioxidative potential of the present invention after heating for 2 h at 120° C.

TBA data was collected by analyzing samples for peroxide value using the TBA (thiobarbituric acid) test described by Tarladgis et al., A Distillation Method for the Quantitative Determination of Malonaldehyde in Rancid Foods, Am. Oil Chemists' Soc. 1960, Vol. 37, pp. 44–48. Samples were stored at 60° C. for a 7-day period and reflect the early stage of the Maillard reaction (in the presence of 10% sucrose or blends of sucrose-sorbitol). During the early stage of nonenzymatic browning (Maillard reaction), colorless products are formed, and further reactions (called the late or advanced stage) give rise to a great variety of compounds, which are desirable in some processes (roasting, baking) but in others (storage, sterilization) may cause undesirable colors and flavors, a reduction in nutritional value, and the production of potentially toxic compounds.

Acid hydrolysis of sucrose is the major cause of increases in reducing sugars. Reducing sugars are not compatible with some embodiments of the antioxidant compositions of the invention (e.g., caseinophosphopeptide-chitosan complex). The fructose-glucose ratio increases at a rate determined by inversion of sucrose. The extent of acid hydrolysis of sucrose is dependent on temperature. The higher the temperature, the higher the extent of acid hydrolysis of sucrose. Hence, in some methods of the present invention, in order to retain the antioxidant activity exhibited by the caseinophosphopeptide-chitosan complex, the extent of acid hydrolysis of sucrose should be within a certain temperature range.

Pasteurization is a conventional process applied to liquid foods (i.e., milk, fruit juices, egg yolks) for destruction of pathogenic (vegetative) bacteria, yeast and fungi. Microbial destruction may be achieved by subjecting liquid foods to 61.1° C. for 4 min, 72° C. for 15 sec or 127° C. for 4 sec. The process of pasteurization minimizes the acid hydrolysis of sucrose in fat emulsions, thereby contributing to the overall antioxidant potential of certain natural ingredients of the present invention (i.e., caseinophosphopeptide-chitosan complex). In the case of fat emulsions prepared with 10% sorbitol, MRPs are not formed after a storage period of 14 days at 60° C. as inferred by the TBA assay method.

Virtually all sugar alcohols share the same type of carbon skeleton with other natural, dietary carbohydrates, and the sugar alcohols can even be assayed as sugars in chemical total sugar analyses. All sugar alcohols can be converted chemically or enzymatically to the corresponding aldoses and ketoses, which in turn are reducible to the sugar alcohol form.

Some of common denominators of sugar alcohols that make them biologically unique are as follows:

The absence of reducing carbonyl groups—This fact makes sugar alcohols chemically somewhat less reactive than the corresponding aldoses and ketoses. The sugar alcohols thus avoid certain chemical reactions that take place at a high rate with several aldoses and ketoses. The relative chemical inertness is also reflected in the fact that in the human oral cavity the sugar alcohols are less reactive and do not normally participate in extensive acid formation in dental plaque.

Complex formation—By virtue of their polyoxy nature, many sugar alcohols form interesting although chemically weak complexes with several polyvalent cations. For various physiologic and nutritional purposes the complexes with $Ca^{2+}$, $Fe^{2+}$, $Fe^{3+}$, $Cu^{2+}$ and possibly several trace elements in general are important.

Hydrophilicity—The presence of the maximum possible number of hydroxyl groups in a carbohydrate structure makes virtually all sugar alcohols very hydrophilic (although the solubility of galactitol and D-mannitol in water is lower). At least some lower homologues can compete with water molecules for the hydration layer of proteins (and peptides), other biomolecules, and also metal cations (without true complex formation). The consequences of this can be seen in the fact that in aqueous solutions the sugar alcohols indirectly strengthen hydrophobic interactions between proteins (and peptides), stabilizing them against thermal and other denaturation or damaging purposes (Mäkinen, K. K. in Internat. Dent. J. 35, 23–35 (1985)). Glucose and sucrose are polyhydric alcohols.

Because of their polyol nature, some sugar alcohols (D-mannitol for example) with the right configuration can act as free radical scavengers in biological and experimental systems (Mäkinen, K. K. in Internat. Dent. J. 35, 23–35 (1985).

Accordingly in certain embodiments of the present invention, the antioxidant compositions include medium-chain triglycerides (MCT), especially caproic (C6.0), caprylic (C:8.0), and capric (C10:0).

The antioxidant compositions may also include polysaccharides such as sulfated polysaccharides. Sulfated polysaccharides may include iota-, kappa-, or lambda-carrageenan, or combinations thereof.

Compositions of the present invention may also include alpha-casein, beta-casein, kappa-casein or protein fragments, glycopeptides, phosphopeptides and combinations thereof. Phosphopeptides may include phosphopeptides high in $alpha_{s2}$-casein and medium-chain triglycerides such as caseinophosphopeptides. Caseinophosphopeptides may be isolated from caprine (goat) milk to produce caprine caseinophosphopeptide. Caseinophosphopeptides have a particularly potent ability to form soluble complexes with calcium.

Antioxidant compositions may further include alpha, beta, gamma or delta tocopherols, alpha, beta, gamma or delta tocotrienols, tocopherols, tocotrienols, beta-carotene, phospholipids, chitosan or combinations thereof.

The antioxidant compositions may also include polyphenols derived from the fruit of *Solanum melongena*.

Fat emulsion particles containing sucrose or sorbitol increase the solubility (and therefore, dispersion) of tocopherol (vitamin E) and beta-carotene (provitamin A) present in flax oil. Fat particles containing sucrose or sorbitol will also increase the solubility (dispersion) of cocoa (polyphenolic compounds), eggplant-carrageenan complex (polyphenolic compounds) and caprine caseinophosphopeptide-chitosan complex. The enhanced antioxidant activity observed in O/W emulsions containing Canadian flaxseed oil stems from the cooperation among tocopherols, beta-carotene, phospholipids, sorbitol, proprietary cocoa mix, and selected antioxidant compositions of the present invention.

Tocopherols are free-radical terminators that interrupt the free-radical chain of oxidative deterioration by contributing hydrogen from the phenolic hydroxyl groups. Beta-carotene functions as a chain-breaking antioxidant. (It does not prevent the initiation of lipid peroxidation, but rather, stops the chain reaction by trapping free radicals, which halts the progression of free radical activity.) TBA data clearly indicate that Organic American flaxseed oil is more susceptible to lipid oxidation than Organic Canadian flaxseed oil. This can be ascribed to the low content of tocopherols and beta-carotene of Organic American flaxseed oils, which are likely derived from Genetically Modified Organisms.

Phospholipids used in embodiments of the invention may include phospholipids from the group of egg yolk, soybean phospholipids, or combinations thereof. TBA studies confirm the synergistic antioxidant effects among soybean phospholipids (lecithin), beta-carotene (provitamin A), tocopherol (vitamin E), and sorbitol (sugar alcohol) or sucrose (non-reducing sugar) in flax oil emulsions. The resulting flax oil emulsions and the further use of soybean phospholipids, sorbitol or sucrose along with homogenization minimize the lipid oxidation of Omega-3, Omega-6, and Omega-9 fatty acids. The shelf life of these essential polyunsaturated fatty acids (Omega-3, Omega-6, Omega-9) in O/W emulsions are therefore greatly extended by some antioxidant compositions of the present invention. Identical benefits are realized with a proprietary cocoa mix and subsequent homogenization.

Lecithin is widely used in lipid-based food products as an antioxidant synergist. The structure of phospholipid molecules enables lecithin to establish a protective coating on the surface of the oil droplet, thereby retarding lipid oxidation. The process of homogenization entraps not only the phospholipid molecules but also the tocopherol and beta-carotene molecules in the oil droplets that result in enhanced protection against lipid oxidation. The production of low-fat products is further improved by the method of incorporating selected antioxidant compositions of the invention and egg yolk phospholipids to impart a rich and creamy mouthfeel characteristic in low-fat products.

The further addition of pH modifiers including citric acid, ascorbic acid, gluconic acid or combinations thereof may improve the oxidative stability. The yet further addition of chelating agents including citric acid may also enhance the oxidative stability. Although citric acid controls the conversion of sucrose to invert sugar, accelerated storage conditions (i.e., a temperature of 60° C. for more than 7 days) can lead to the formation of invert sugar (a mixture of glucose and fructose).

In a specific embodiment, the invention includes an antioxidant microemulsion or nanoemulsion composition having ingredients selected from the group of: non-reducing sugars, sugar polyols, or combinations thereof; modified starches; polysaccharides; glycerides selected from enzymatically modified oils, fats, and fatty acids of mono-, di-, and tri-glycerides; glycerides selected from lipolyzed modified oils, fats, and fatty acids of mono-, di-, and tri-glycerides; fruit concentrate sweetener as humectant that comprises a blend of hydrolyzed starch having a dextrose equivalent (D.E.) of up to approximately 25; fruit juice or fruit syrup concentrate of at least approximately 40% soluble solids and approximately 0% insoluble solids thereby forming a liquor having a dry weight composition of approximately 40 to approximately 65% complex carbohydrates; and approximately 35 to approximately 55% simple sugars from the fruit juice or fruit syrup concentrate; and approximately 0 to approximately 5% nutritional components occurring naturally in the fruit juice or fruit syrup concentrate; cocoa powder; Sucralose; or combinations thereof.

Cocoa powder contains around 20% raw protein. Maillard reactions are initiated by a condensation between the free amino group of amino acid, peptide, or protein and the carbonyl group of a reducing sugar to give a N-substituted glycosyl-amino compound followed by the reversible formation of the Schiff base, which cyclizes to the NB substituted glycosylamine and its then converted into the Amadori compound. The Amadori rearrangement is catalyzed by weak acids and is considered the key step of the Maillard reaction. Amadori compounds formed during the early stage of the Maillard reaction are responsible for the loss of nutritional value of amino acids and proteins, because their biological activity is reduced by the formation of Amadori compounds. Cocoa powder also contains around 10% polyphenols, which have antioxidative effects (Dreosti I. E. in Nutrition 16, 692–694 (2000)). The ability of cocoa powder to inhibit lipid oxidation in O/W emulsion systems with added sucrose (pH 6.6) is influenced by heat treatments. An extensive acid hydrolysis of sucrose, by heat, is detrimental to the antioxidant capacity of cocoa powder. However, for formulated O/W emulsions that have sorbitol (pH 6.6), cocoa powder shows enhanced oxidative stability upon storage at 60° C. for 28 days.

Pasteurization heating provides a means to minimize the acid hydrolysis of sucrose in fat emulsions. Thus, pasteurized flax oil emulsions including a proprietary cocoa mix, soybean phospholipids, sorbitol or sucrose along with homogenization minimize the lipid oxidation of Omega-3, Omega-6, and Omega-9 fatty acids. The shelf life of these essential polyunsaturated fatty acids (Omega-3, Omega-6, Omega-9) in O/W emulsions may therefore be greatly extended with the proprietary cocoa mix. The combination of antioxidant compositions of the invention and/or the proprietary cocoa mix demonstrates additional synergistic effects.

A wide range of products may be manufactured by inclusion of the antioxidant compositions of the invention including: hypercholesterolemia prevention products in a mammal including salts selected from the group of calcium and magnesium salts; bone mineral loss prevention products in a mammal including salts selected from the group of calcium and magnesium salts; oils rich in Omega-3 products, further comprised of salts selected from the group of calcium and magnesium salts; oil-soluble flavor products; oil-soluble vitamin, nutraceutical, or pharmaceutical products; products having vegetable oils including rice bran oil, flax, chia, hemp, castor, soybean, lesquerella, dehydrated castor oil, rich in Omega-3, or conjugated linoleic acid, animal oils including fish, egg, poultry, and beef oils rich in Omega-3, or conjugated linoleic acid, or combinations thereof; beverage products being transparent including salts selected from the group of calcium and magnesium salts; cocoa products having improved creaminess, reduced bitterness, and reduced oxidation; protein rich products including high-methoxyl pectins or pectin alginates or combinations thereof having reduced protein settling and sedimentation; protein rich products having reduced protein settling and sedimentation; oil-in-water micro- and nano-emulsions having increased emulsion and oxidation stability; or water-in-oil micro- and nano-emulsions having increased emulsion and oxidation stability.

The range of products include, but are not limited to, confectionery, baked goods, spreads, dressings, salad dressings, nutraceutical supplements, functional foods products, ice cream, seed milks, dairy products, pharmaceutical tablets, syrups, and medicines, functional confectionery products, and mineral-enriched drinks.

Compositions of the present invention may include O/W and W/O emulsions prepared with vegetable and animal oils that contain a significant amount of highly polyunsaturated fatty acids such as rice bran oil, flaxseed oil, chia oil, hemp oil, soybean oil, lesquerella oil, castor oil, dehydrated castor oil, menhaden oil, sardine oil, herring oil, salmon oil, anchovy oil, and other oils rich in Omega-3, or conjugated linoleic acid. The oil content of the OW and W/O emulsions may vary according to the oil species component used and other components but may be within the range of 0.1–95 w/v %, preferably 1–85 w/v %. Embodiments of the present invention also may be effective when applied to oil flavors such as fruit and herb flavored oils, cheese flavored oils, butter flavored oils, and oil soluble vitamin, nutraceutical or pharmaceutical products.

Oil-in-water (O/W) emulsions that include small lipid droplets dispersed in an aqueous medium form the basis of many kinds of foods, e.g., milk, cream, beverages, dressings, dips, sauces, batters and deserts. Emulsions are thermodynamically unstable systems because of the unfavorable contact between oil and water phases, and because the oil and water phases have different densities, hence they will always breakdown over time. Use of emulsifiers, which are surface-active ingredients that absorb to the surface of freshly formed lipid droplets during homogenization, usually retards emulsion breakdown. Once absorbed, they facilitate further droplet disruption by lowering the interfacial tension, thereby reducing the size of the droplets produced during homogenization. Emulsifiers also reduce the tendency for droplets to aggregate by forming protective membranes and/or generating repulsive forces between the droplets. A good emulsifier should rapidly adsorb to the surface of the lipid droplets formed during homogenization, rapidly lower the interfacial tension by a significant amount and protect the droplets against aggregation during emulsion processing, storage and utilization.

Emulsions prepared with egg yolk phospholipids and the antioxidant compositions of the present invention have improved stability against phase separation and particle aggregation. Recent studies for the purpose of enhancing flavor release have shown that the release of non-polar flavors from O/W emulsions during mastication is controlled by encapsulating the oil droplets within biopolymer particles (Malone et al. in Flavor Release, ACS Symposium Series, American Chemical Society, pp. 212–217 (2000)). This approach can be used to create low-fat food products with similar flavor release characteristics to high-fat food products (Malone et al. in Flavor Release, ACS Symposium Series, American Chemical Society, pp. 212–217 (2000)). The referenced method for enhancing flavor release is demonstrated by antioxidant compositions of the present invention for producing enhanced oxidative stability. Biopolymer particles are created by the caprine caseinophosphopeptide-chitosan complex and eggplant-carrageenan complex that are embodiments of the inventive antioxidant compositions.

The caseinophosphopeptide employed as antioxidant compositions of the present invention may include $alpha_{s2}$-casein as isolated from caprine (goat) milk. Caseins and caseinophosphopeptides exhibit different degrees of phosphorylation, and a direct relationship between the degree of phosphorylation and mineral chelating activity has been described (Kitts, D. D. in Can. J. Physiol. Pharmacol. 72, 423–434 (1994)). Accordingly based on phosphorylation, $alpha_{s2}$-casein>$alpha_{s1}$-casein>beta-casein>kappa-casein. Caseinophosphopeptide isolated from caprine (goat) milk high in $alpha_{s2}$-casein ($alpha_{s2}$-casein=29.2% of total casein) has more mineral chelating activity than a caseinophosphopeptide isolated from bovine (cow) milk ($alpha_{s2}$-casein=12.1% of total casein). The phosphoric group of phosphoserine and carboxic groups of acidic amino acids present in the caseinophosphopeptide isolated from caprine (goat) milk high in $alpha_{s2}$-casein, without being bound by theory, likely complexes with pro-oxidative metal ions such as iron and copper. It would be understood to one skilled in the art that other milk high in $alpha_{s2}$-casein may be suitable for the present invention. Choice of milk may be influenced, inter alia, by economic factors and availability of particular milk. The selection of milk containing high levels of alpha$_{s2}$-casein, which is low in alpha$_{s1}$-casein, may be carried out by reversed-phase high performance liquid chromatography (RP-HPLC) (Mora-Gutierrez et al. in J. Dairy Sci. 74, 3303–3307 (1991)). The casein composition of the caprine caseinophosphopeptide is normally as follows: alpha$_{s2}$-casein content=29.2%, alpha$_{s1}$-casein content=5.9%; beta-casein content=50.5% and kappa-casein content=14.4%.

The fat in caprine (goat) milk is also rich in medium-chain triglycerides (MCT) (C6:0 Caproic, C8:0 Caprylic and C10:0 Capric) which are absorbed in the proximal intestine and do not require bile salts to be absorbed (Vanderhoof et al. in J. Parenter. Enteral Nutr. 8, 685–689 (1984)). These MCT have become of considerable interest to the medical profession because of their unique benefits in many metabolic diseases of humans (Babayan V. K. in J. Amer. Oil Chem. 59, 49A–51A (1981)). The bone (femur and sternum) is the preferential organ for the deposit of magnesium in animals fed a caprine (goat) milk diet, which has been ascribed to its special characteristics concerning lipid composition (rich in MCT) (Lopez-Alliaga et al. in J. Dairy Sci. 86, 2958–2966 (2003)). Lipids are associated with proteins (caseins) in milk and their content in bound lipid fractions is high (Cerbulis J. in J. Agric. Food Chem. 15, 784–786 (1967)). The MCT content of the caprine caseinophosphopeptide used in this inventive antioxidant composition is high because this caprine caseinophosphopeptide is produced from caprine (goat) milk with a fat content of 1% by enzymatic hydrolysis and acid precipitation with chitosan. Chitosan, which assumes a polycationic character at acidic pH, exhibits a high fat-binding capacity (No et al. in J. Food Sci. 65, 1134–1137 (2000)).

In an exemplary embodiment of the invention, caprine (goat) milk (1% fat content) characterized by a high alpha$_{s2}$-casein content is used as the starting material in a method of the present invention: (a) digesting the casein present in caprine (goat) milk high in alpha$_{s2}$-casein with 0.01% (w/v) trypsin at a substantially neutral pH to produce a crude caseinophosphopeptide, (b) reducing the pH to 4.5 with 2% (w/v) chitosan (SEACURE L 110 with 70% deacetylation; Pronova Biopolymer, Inc., Oslo, Norway) dissolved in 10% citric acid (w/v), (c) removing the unreacted casein from the supernatant by centrifugation, (d) permitting the supernatant to stand for 20 hours at 4° C., (e) adjusting the pH of the supernatant to about 6.0, then adding calcium chloride (0.2% w/v) and ethanol (40% v/v), to precipitate a calcium-bound caseinophosphopeptide, which is recovered by centrifugation. This calcium-bound caseinophosphopeptide may be washed with deionized water and dried by lyophilization. The composition of the lyophilized product is provided in Table 1.

TABLE 1

| Caprine caseinophosphopeptide composition | Per 100 grams |
|---|---|
| Kjeldahl N | 6.49 |
| Calcium | 8.61 |
| Phosphorus | 2.76 |
| Medium-chain triglycerides | 9.71 |

A food grade acidulent may be added to the fat emulsion before adding the acid-soluble caprine caseinophosphopeptide. The acid-soluble caprine caseinophosphopeptide may be added to an acidic environment ranging from approximately pH 2.0 to 5.7. The food grade acidulent may be citric acid, ascorbic acid, gluconic acid, and mixtures thereof. The acidulent in the fat emulsion may be mostly citric acid. Citric acid sequesters deleterious trace metals, particularly copper and iron, which hasten deterioration of color, flavor and vitamin A content.

As used herein, the term LBJ refers to a mixture of sugars and soluble fiber derived from eggplant (*Solanum melongena*). To produce LBJ in one example, whole eggplant is slurried with water to which citric acid and iota-carrageenan are added. This mixture is reacted at elevated temperature under controlled conditions for a specific period of time. The resulting slurry of sugars/soluble fiber (LBJ) is subsequently treated with an adsorptive resin functional to remove from the sugars/soluble fiber (LBJ) bitter taste components, color and odor components. The treated sugars/soluble fiber (LBJ) solution may be concentrated and dried if desired to powder form. The further addition of polyphenols, specifically the polyphenols derived from the fruit of *Solanum melongena* is possible.

More specifically, in an exemplary embodiment, an aqueous solution containing 0.50% citric acid and 0.25% iota-carrageenan is heated at 45° C. for 6 hours with continuous stirring. Eggplant samples may be obtained from local food stores or any other source and stored under refrigeration at approximately 4° C. until use if necessary. About one hour prior to use, the eggplant samples are removed from refrigeration and equilibrated at room temperature at about 22° C. The eggplants (0.7 kg) are rinsed with water, peeled and then sliced into 4–5 mm thick slices. These are immediately immersed in a treatment bath containing the mixed-acid solution of citric acid and iota-carrageenan. The treatment bath with the sliced eggplants and mixed-acid solution of citric acid and iota-carrageenan is then heated to a temperature that may be in the range 70° C. to 80° C., typically 75° C. This elevated temperature may be maintained for at least 2 hours but possibly held at such elevated temperature for longer, e.g., about 4 hours, and then cooled to between 0° C. and 50° C., in a particular embodiment about 4° C., for a period of time, typically about 12 hours. Finally, the mixture is decanted through Whatman No. 4 filter paper or similar filtration medium.

In an exemplary embodiment, the aqueous slurry/solution (LBJ) is passed through a column of an adsorptive resin. The adsorptive resin may be a polymeric resin, which functions to remove bitterness, odor and color from the aqueous slurry/solution (LBJ). One suitable class of adsorptive resins for use are polymeric cross-linked resins composed of styrene and divinylbenzene such as, for example, the Amberlite series of resins, e.g., Amberlite XAD-2, Amberlite XAD-4 and Amberlite XAD-16, which are available commercially from Supelco of Bellefonte, Pa. Other polymeric crosslinked styrene and divinylbenzene adsorptive resins suitable for use according to the invention are XFS-4257, XFS-4022, XUS-40323 and XUS-40322 manufactured by Dow Chemical Company of Midland, Mich., and other similar resins.

Treatment of the aqueous slurry/solution (LBJ) in accordance with this invention may be conducted in various manners such as by a batch treatment or by passing the aqueous slurry/solution (LBJ) through a column containing the adsorptive resin. The column size selected depends upon the sample size and the concentration of the aqueous slurry/solution (LBJ).

More specifically, in an exemplary embodiment, a batch of approximately 100 g of Amberlite XAD-2 is slurried in water and poured into an open glass chromatography column (2×30 cm) fitted with a Teflon stopcock. The column is then prepared for use by washing it with two liters of twice-distilled water, two liters of distilled methanol (reagent grade), and finally two liters of distilled water. The aqueous slurry/solution (LBJ) treated in the column may preferably be free of insoluble material so as to not plug the column or impede flow. Generally, the concentration of eggplant undergoing treatment may be in the range of about 50 to 70% by weight. The pH of the slurry/solution (LBJ) may be in the range of pH 3 to 4. The flow rate of the aqueous slurry/solution (LBJ) through the column may preferably be slow enough to allow sufficient time for the undesired bitterness, color and odor to be adsorbed in the adsorptive resin. Column flow rates between one to five bed volumes/hour are generally satisfactory.

One aqueous slurry/solution (LBJ) according to the present invention contains a fructose portion of 3.7% and a sucrose portion of 1.5% as determined by high-performance liquid chromatography (HPLC). Thus, this natural composition exhibits a high hygroscopic property. Saccharide polymers may be used as spray-drying aids in the manufacture of this natural composition. The composition may include between around 5 and 10% by weight maltodextrin. The maltodextrin may have a low DE, generally not exceeding about 10. The aqueous slurry/solution (LBJ) is mixed with maltodextrin DE=10 at a concentration of 6% (by weight) after the aqueous slurry/solution (LBJ) is passed through a column of the adsorptive resin. Then, the aqueous slurry/solution (LBJ 10) is dried by spray drying or the like to provide a product that is well suited for use as a natural antioxidant ingredient for fat emulsions. The composition of this product is provided in Table 2.

TABLE 2

| LBJ 10 physicochemical composition | Per 100 grams |
|---|---|
| carbohydrate portion | 92.21 |
| nitrogen content | 0.71 |
| fat portion | 0.16 |
| ash portion | 2.33 |
| dietary fiber portion | 0.41 |
| soluble fiber portion | 0.41 |
| fructose portion | 3.72 |
| glucose portion | 4.26 |
| sucrose portion | 1.48 |
| maltose portion | 2.19 |
| sugar portion | 11.65 |

The numerical values for carbohydrate, crude protein, fat portion, ash portion, dietary fiber portion, soluble fiber portion, and sugar portion are those according to a general analysis.

Carrageenans exhibit thickening or viscosity-increasing effect. The viscosity of the LBJ 10 composition of Table 2, which has 0.25% iota-carrageenan, is rather low, i.e., about 11 cps (1%, 22° C.), and it tastes slightly sweet and is odorless. Carrageenans such as kappa-carrageenan and lambda-carrageenan can also be used in the preparation of LBJ 10. Carrageenans are known to interact with casein (and derived phosphopeptides) to modify food texture by improving water holding capacity (Mora-Gutierrez et al. in J. Agric. Food Chem. 46, 4987–4996 (1998)). In some embodiments of the invention, the combination of egg yolk phospholipids, caprine caseinophosphopeptide and LBJ 10 impart richness, lubricity and creaminess to fat-reduced emulsions. Because antioxidant activities are correlated with the phenolic contents of foods, the total phenolic content of LBJ 10 was determined using methods described by Singlenton et al., Analysis of Total Phenols and Other Oxidation Substrates and Antioxidants by Means of Folin-Ciocalteu Reagent, Methods in Enzymology, Oxidants and Antioxidants, 1998, pp. 152–178. The total phenolic content of LBJ 10 was 45 μmol gallic acid equivalents/g of LBJ 10.

The present invention includes compositions of natural antioxidants including tocopherols, beta-carotene, egg yolk or soybean phospholipids, sucrose or sorbitol, caprine caseinophosphopeptide, eggplant (LBJ 10), and citric acid.

Specific antioxidant ingredients of the present invention may include from about 0.01 to about 0.03% by lipid content of tocopherols, from about 0.01 to about 0.03% by lipid content of beta-carotene, from about 0.05 to about 0.5% by weight of emulsion of egg yolk or soybean phospholipids, from about 2 to about 20% by weight of emulsion of sucrose or sorbitol, from about 0.01 to about 0.05% by weight of emulsion of caprine caseinophosphopeptide, from about 0.01 to about 0.2% by weight of emulsion of eggplant (LBJ 10), and from about 0.05 to about 0.5% by weight of emulsion of citric acid.

One specific composition includes about 0.01% tocopherols, 0.01% beta-carotene, 0.1% egg yolk or soybean phospholipids, 10% sorbitol, about 0.05% caprine caseinophosphopeptide, about 0.1% eggplant (LBJ 10), and about 0.5% citric acid, all by weight of emulsion.

Unrefined Canadian flaxseed oil is rich in tocopherols and beta-carotene. A specific embodiment of the composition of the present invention, especially effective for O/W emulsions prepared with Canadian flaxseed oil, is as follows: 0.05% caprine caseinophosphopeptide, 0.1% eggplant (LBJ 10), and 0.5% citric acid.

The fat emulsion may be produced by conventional technology. An exemplary production process includes adding egg yolk or soybean phospholipids in suitable amounts to a predetermined amount of the oil component, homogenizing the mixture, adding sorbitol, caprine caseinophosphopeptide, eggplant (LBJ 10),and citric acid in suitable amounts to a predetermined amount of the water component, and emulsifying the entire mixture with a homogenizing machine such as the conventional homo-mixer, homogenizer, ultrasonic homogenizer, or pressure homogenizer. The mixture may preferably be finely dispersed by homogenization to ensure a homogeneous equal dispersion of the natural antioxidant composition in all the oil particles. The average particle diameter of the fat emulsion particles is within the range of 5–50 nm. The emulsified mixture may be pasteurizated using conventional methods.

Some natural antioxidant compositions of the present invention may exhibit antioxidant activity superior to prior compositions or synthetic antioxidants. Some natural antioxidant compositions of the present invention may also offer a number of health benefits, including helping to promote bone health by boosting calcium and magnesium absorption, and a healthy cardiovascular system by lowering blood serum cholesterol levels. Thus in certain embodiments, the amount of caprine caseinophos-phopeptide and eggplant (LBJ 10) may range from the minimum amount which will stabilize the oil against oxidation, or effectiveness, to at least that amount which will promote bone health and protect against heart disease in animal or human bodies. In general, the amount of caprine caseinophosphopeptide and eggplant (LBJ 10) used may range from 0.01 to 0.05% by weight for caprine caprine caseinophosphopeptide and 0.01% to 0.1% by weight for eggplant (LBJ 10).

EXAMPLES

The following examples are included to demonstrate specific embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

Examples 1 through 3 demonstrate that a specific composition of the present invention is superior to prior compositions of synthetic antioxidants in the prevention of rancidity in O/W emulsions containing highly polyunsaturated lipids. After 28 days of storage, thiobarbituric acid (TBA) value was determined as an index of oxidation stability of the composition.

The health benefits of some embodiments of the present invention are explained in detail in Examples 4 through 6.

The materials used in these examples were as follows: Flaxseed oil containing high levels of tocopherols and beta-carotene: an unrefined flaxseed oil, supplied under the trade name of Huile de Lin by Gold Top Organics, Edmonton, AB, Canada. Soybean phospholipids: powered soybean lecithin containing 40% phosphathidylserine under the trade name of LECI-PS 40 P, supplied by Lucas Meyer, Inc., Decatur, Ill. Egg yolk phospholipids: powered egg yolk lecithin containing 60% phosphathidylcholine, supplied by Sigma Chemical Company, St. Louis, Mo. Propyl gallate supplied by Sigma Chemical Company, St. Louis, Mo. Hydrosoluble Rosemary powered extract was supplied by Biolandes Aromes, Boulogne, France. A proprietary cocoa mix comprised of alkaline cocoa powder (approx. 14% cocoa butter), fruit juice and grain dextrins, modified starch, modified cocoa butter, and Sucralose.

Example 1

O/W Emulsion Containing Sorbitol and Egg Yolk Phospholipids

Flaxseed oil (30 mL), sorbitol (10 g), egg yolk phospholipids (0.1 g), hemoglobin (0.02 g), and deionized water (59.88 mL) were homogenized for 5 minutes with a Bio-homogenizer Mixer (Biospec Products, Inc., Bartlesville, Okla.). This oil-in-water (O/W) emulsion was used as the control (Sample A). Sample B was produced through the addition of 0.05% caprine caseino-phosphopeptide, 0.1% eggplant (LBJ 10), and 0.5% citric acid to an aliquot of 50 mL of the O/W emulsion. Sample B was homogenized for 5 minutes. Samples C and D were made through the addition of 0.01% propyl gallate and hydrosoluble rosemary powered extract, respectively. Samples C and D were homogenized for 5 minutes.

Samples were stored in glass test tubes secured with Teflon-lined screw caps. After a storage period of 28 days at 60° C., the samples were evaluated as to peroxide content. A 60° C. temperature hastened the rate of oxidation and at the same time encouraged progression of ambient temperature oxidative mechanisms and minimized artifact forming reactions. (See Frankel E. N., In Search of Better Methods to Evaluate Natural Antioxidants and Oxidative Stability in Food Lipids, Trends in Food Sci. Technol. 1993, Vol. 4, pp 220–225.) Because lipid peroxidation catalyzed by heme-proteins (e.g., hemoglobin, cytochrome C, myoglobin) in a basic deteriorative and pathological reaction, the effectiveness of the invention to prevent such peroxidation was evaluated. Samples were analyzed for the peroxide value using the TBA (Thiobarbituric acid) test described by Tarladgis et al., A Distillation Method for the Quantitative Determination of Malonaldehyde in Rancid Foods, Am. Oil Chemists' Soc. 1960, Vol. 37, pp. 44–48. Measurements were taken at 14-day intervals. The antioxidant activity of the composition according to an embodiment of the present invention is demonstrated by the results in Table 3.

TABLE 3

| Sample | 14 days<br>TBA (O.D. 538/g) | 28 days<br>TBA (O.D. 538/g) |
| --- | --- | --- |
| A | 0.128 | 0.065 |
| B | 0.051 | 0.018 |
| C | 0.076 | 0.040 |
| D | 0.089 | 0.047 |

As is apparent from the data, the antioxidative activity of the composition according to an embodiment of the present invention (Sample B) is superior to the activities exhibited by the synthetic antioxidant propyl gallate and the natural antioxidant rosemary extract (Samples C and D, respectively). The enhanced activity likely stems from the cooperation among tocopherols, beta-carotene, phospholipids, sorbitol, caprine caseinophosphopeptide, eggplant (LBJ 10), and citric acid. It should be noted that the addition of egg yolk phospholipids and sorbitol and the process of homogenization actually decrease oxidation of the O/W emulsion (Sample A).

Example 2

O/W Emulsion Containing Sorbitol and Soybean Phospholipids

Flaxseed oil (30 mL), sorbitol (10 g), soybean phospholipids (0.1 g), hemoglobin (0.02 g), and deionized water (59.88 mL) were homogenized for 5 minutes with a Bio-homogenizer Mixer (Biospec Products, Inc., Bartlesville, Okla.). This oil-in-water (O/W) emulsion was used as the control (Sample A). Sample B was produced through the addition of 0.05% caprine caseinophosphopeptide, 0.1% eggplant (LBJ 10), and 0.5% citric acid to an aliquot of 50 mL of the O/W emulsion. Sample B was homogenized for 5 minutes. Samples C and D were made through the addition of 0.01% propyl gallate and hydrosoluble Rosemary powered extract, respectively. Samples C and D were homogenized for 5 minutes.

Samples were stored in glass test tubes secured with Teflon-lined screw caps. After a storage period of 28 days at 60° C., the samples were evaluated as to peroxide content. The antioxidant effectiveness was evaluated by the chemical TBA (thiobarbituric acid) method following as general guideline the procedure of Tarladgis et al. 1960. J. Ame. Oil Chem. Soc. 37:44. The results given in Table 4 show clearly the superior antioxidant activity of the composition according to an embodiment of the present invention.

TABLE 4

| Sample | 14 days TBA (O.D. 538/g) | 28 days TBA (O.D. 538/g) |
|---|---|---|
| A | 0.151 | 0.087 |
| B | 0.063 | 0.026 |
| C | 0.089 | 0.059 |
| D | 0.094 | 0.061 |

Example 3

A Chocolate-Flavored, O/W Emulsion Containing Sorbitol and Egg Yolk Phospholipids Cocoa mix (2 g), flaxseed oil (30 mL), sorbitol (10 g), egg yolk phospholipids (0.1 g), hemoglobin (0.02 g), and deionized water (57.88 mL) were homogenized for 5 minutes with a Biohomogenizer Mixer (Biospec Products, Inc., Bartlesville, Okla.). This oil-in-water (O/W) emulsion was used as the control (Sample A). Sample B was produced through the addition of 0.05% caprine caseinophosphopeptide, 0.1% eggplant (LBJ 10), and 0.1% citric acid to an aliquot of 50 mL of the O/W emulsion. Sample B was homogenized for 5 minutes. The pH of Sample B was lowered from about 6.6 to 5.7. Note that the pH was maintained above the point of protein denaturation, precipitation. Samples C and D were made through the addition of 0.01% propyl gallate and hydrosoluble rosemary powered extract, respectively. Samples C and D were homogenized for 5 minutes.

Samples were stored in glass test tubes secured with Teflon-lined screw caps. After a storage period of 28 days at 60° C., the samples were evaluated as to peroxide content. The antioxidant effectiveness was evaluated by the chemical TBA (thiobarbituric acid) method following as general guideline the procedure of Tarladgis et al. 1960. J. Ame. Oil Chem. Soc. 37:44. The results of the addition of cocoa to the O/W emulsions in the absence and presence of a composition according to an embodiment of the present invention and commercial antioxidants are summarized in Table 5.

TABLE 5

| Sample | 14 days TBA (O.D. 538/g) | 28 days TBA (O.D. 538/g) |
|---|---|---|
| A | 0.112 | 0.058 |
| B | 0.045 | 0.012 |
| C | 0.067 | 0.033 |
| D | 0.078 | 0.046 |

The addition of cocoa significantly reduced the level of peroxides in all the O/W emulsions (samples A thru D), while the addition of a composition according to an embodiment of the present invention (sample B) was more effective in reducing peroxides than the addition of propyl gallate or rosemary extract (samples C and D, respectively).

Example 4

Cholesterol-Lowering Activity in Rats

Rats (Sprague-Dawley type, 7 weeks of age, male) were fed a diet low in calcium and high in animal fat. These rats were divided into three groups each being formed of 12 rats having a similar mean body weight of 200–205 grams, then three kinds of heat-sterilized O/W emulsions i.e., an O/W emulsion of 0.05% (w/v) caprine caseinophosphopeptide and 0.01% (w/v) eggplant (LBJ 10) supplemented with calcium (300 ppm), an O/W emulsion supplemented with calcium (300 ppm), and an O/W emulsion non-supplemented with calcium were respectively given from feeding bottles to the rats as drinking water. Composition of these O/W emulsions was identical in terms of flaxseed oil (1 g/L), soybean phospholipids (0.1 g/L), sucrose (4 g/L), and citric acid (5.0 g/L) content. O/W emulsions were supplemented with calcium gluconate (3 g/L).

The three groups of rats were free to take the feed and water in, during the treatment period of 21 days. At the end of the 21-day, rats were deprived of food overnight and anesthetized by intraperitoneal injection of sodium pentobarbital (40 mg/kg body weight). Blood collection was carried out from cardiac puncture. With respect to analysis, measurements were carried out using a DU-530 Spectrophotometer made by Beckman by means of a colorimetric method.

Results of the measurement for blood serum total cholesterol are shown in Table 6.

TABLE 6

| Group | Cholesterol, mg/dL |
|---|---|
| Control (non-supplemented) | 84.92 ± 7 |
| Control (supplemented) | 78.36 ± 5 |
| Natural antioxidant composition (supplemented) | 67.30 ± 4 |

According to the above results, it has been proved that the increase in serum cholesterol of male Sprague-Dawley rats fed a low calcium and high animal fat diet has been lowered by the addition of an antioxidant composition according to an embodiment of the present invention (caprine caseinophosphopeptide combined with eggplant (LBJ 10) and citric acid at levels of 0.05% (w/v), 0.01% (w/v), and 0.5% (w/v), respectively) to a calcium-supplemented O/W emulsion.

This natural antioxidant composition, therefore, can be applied to O/W emulsions as physiologically functional factor.

Example 5

Calcium and Magnesium Bioavailability in Rats

Rats (Sprague-Dawley type, 7 weeks of age, male) were fed an egg white-diet low in calcium. Chromic oxide ($Cr_2O_3$, 0.5 g/kg diet), an insoluble and unabsorbed marker, was added to the egg white-diet to allow estimation of apparent Ca and Mg absorption by determining the ratio of Ca:Cr and Mg:Cr in the diet and feces. These rats were divided into four groups each being formed of 12 rats and having a similar mean body weight of 200–205 grams, then three kinds of heat-sterilized O/W emulsions i.e., an OW emulsion of 0.05% (w/v) caprine caseinophospho-peptide and 0.01% (w/v) eggplant (LBJ 10) supplemented with calcium (300 ppm), an O/W emulsion supplemented with calcium (300 ppm), and an O/W emulsion non-supplemented with calcium were respectively given from feeding bottles to the rats as drinking water. Composition of these O/W emulsions was identical in terms of flaxseed oil (1 g/L), soybean phospholipids (0.1 g/L), sucrose (4 g/L), and citric acid (5.0 g/L) content. O/W emulsions were supplemented with calcium gluconate (3 g/L).

The three groups of rats were free to take the feed and water in, during the treatment period of 21 days. Food intake was measured every day. Feces were collected during the last 3 days and freeze-dried. At the end of the 21-day, rats were deprived of food overnight and anesthetized by intraperitoneal injection of sodium pentobarbital (40 mg/kg body weight). The right femurs were excised for measurement of Ca, and Mg content. The amounts of Ca, Mg, and Cr in the diets and feces were quantified by atomic absorption spectrometry (Varian Analytical Instruments, Walnut Creek, Calif.) after wet-ashing with an acid mixture (16 mol/L $HNO_3$:9 mol/L $HClO_4$=3:1). The right femurs were treated with 1N $HNO_3$ and ashed at 550° C. Ca and Mg content were determined in the same manner as in the case of the diets and feces. Apparent Ca absorption was calculated by the following formula: Apparent Ca absorption (%)=100[(Ca intake/Cr intake)−(Ca in the feces/Cr in the feces)]/(Ca intake/Cr intake). Apparent Mg absorption was calculated in a similar manner.

The apparent Ca and Mg absorption, and femoral bone Ca and Mg content of rats fed the three different O/W emulsions are shown in Table 7.

TABLE 7

| Group | Apparent Ca absorption (%) | Apparent Mg absorption (%) | Bone Ca content (mg/femur) | Bone Mg absorption (mg/femur) |
|---|---|---|---|---|
| Control (non-supplemented | 49 ± 5.7 | 51 ± 4.2 | 89.63 ± 0.27 | 4.47 ± 0.13 |
| Control (supplemented) | 54 ± 6.0 | 49 ± 5.1 | 97.08 ± 0.19 | 4.31 ± 0.27 |
| Antioxidant Composition (supplemented) | 59 ± 5.0 | 61 ± 5.9 | 103.20 ± 0.14 | 5.62 ± 0.11 |

The data show enhanced Ca and Mg bioavailability from the O/W emulsion containing an antioxidant composition according to an embodiment of the present invention.

Example 6

Bone Metabolism and Dynamic Strength of Bone in Rats

Rats (Sprague-Dawley type, 7 weeks of age, male) were fed a diet low in calcium. These rats were divided into four groups each being formed of 12 rats and having a similar mean body weight of 200–205 grams, then three kinds of heat-sterilized O/W emulsions i.e., an O/W emulsion of 0.05% (w/v) caprine caseinophosphopeptide and 0.01% (w/v) eggplant (LBJ 10) supplemented with calcium (300 ppm), an O/W emulsion supplemented with calcium (300 ppm), and an O/W emulsion non-supplemented with calcium were respectively given from feeding bottles to the rats as drinking water. Composition of these O/W emulsions was identical in terms of flaxseed oil (1 g/L), soybean phospholipids (0.1 g/L), sucrose (4 g/L), and citric acid (5.0 g/L) content. O/W emulsions were supplemented with calcium gluconate (3 g/L).

The three groups of rats were free to take the feed and water in, during the treatment period of 21 days. At the end of the 21-day, rats were deprived of food overnight and anesthetized by intraperitoneal injection of sodium pentobarbital (40 mg/kg body weight). The left femurs were collected from the animals and soft tissue was removed. The left femur from each animal was subjected to bone mineral content (BMC), bone mineral density (BMD), and bone mechanical strength (BMS) measurements using dual-energy X-ray absorptiometry (DEXA), which is a typical method used to study the status of bone growth. Table 8 shows the beneficial effects of an antioxidant composition according to an embodiment of the present invention on bone metabolism and dynamic strength of bone in rats.

TABLE 8

| Group | BMC (g/cm) | BMD (g/cm$_2$) | BMS (kg force) |
|---|---|---|---|
| Control (non-supplemented) | 0.1912 ± 0.012 | 0.1346 ± 0.004 | 8.402 ± 320.8 |
| Control (supplemented) | 0.2041 ± 0.012 | 0.1432 ± 0.004 | 8.591 ± 298.02 |
| Antioxidant composition | 0.2134 ± 0.012 | 0.1518 ± 0.004 | 9.567 ± 297.05 |

The data clearly indicate that the O/W emulsion containing an antioxidant composition according to an embodiment of the present invention strengthens the femur bones in rats by enhancing the amount of magnesium retained in bone (Example 5), and that this results from increased apparent magnesium absorption (Example 5).

The caprine caseinophosphopeptide-chitosan-MCT bound complexes, which are present in the above antioxidant composition according to an embodiment of the present invention, are thermally stable and deliver large amount of magnesium to the proximal intestine, the site for magnesium absorption. Thus the complexes per se can provide physiological activity of magnesium to low-pH, protein-based beverages and transparent beverages processed by heat treatment. The complexes prevent protein sedimentation in low pH (3.5–4.2) beverages when used in combination with high-methoxyl pectins or pectin alginates.

Example 7

Transparent Low-pH (3.0–4.2) Beverages Containing Caprine Caseinophosphopeptide

A big factor in the drop in calcium and magnesium consumption in the US is the fact that soft drinks have replaced milk in the American diet. Milk is an excellent source of calcium (1,310 mg/L) and also contains magnesium (120 mg/L). A Consumer Beverage Consumption study conducted in late 2000, surveyed a total of 1,379 participants in two age groups-adults (19–64; 320 males/358 females) and teens (12–18; 326 boys/375 girls). Adults reported that their favorite beverage is "cold, refreshing, and satisfying" whereas teens prefer their drinks to be "cold, refreshing, and delicious". In this survey, teens and adults, milk drinkers and non-milk drinkers expressed comments regarding their concern with health issues, additives, chemicals, handling and spoilage.

A growing body of research now shows that the more soft drinks teenagers consume, the higher their risk of broken bones and, in later life, osteoporosis. Since 1970 Americans have more than doubled their soft drink consumption while drinking less milk. Consumers want a cold, refreshing, satisfying, portable, and healthy beverage. Caprine caseinophosphopeptide can be used in transparent low-pH (3.0–4.2) beverages fortified with calcium and magnesium to prevent the loss of these minerals from bone and therefore, lowering the risk of bone fractures.

Caprine caseinophosphopeptide can also form the building stones for mineral-fortified, low-pH beverages tailored for individuals with lactase non-persistence, a reduced capacity to metabolize lactose. The presence of lactose in milk is detrimental for those individuals that suffer from lactose intolerance. The ingestion of one to two glasses of milk can lead to abdominal discomfort and diarrhea in such individuals. Many studies have noted racial differences in the incidence of lactose intolerance. In the United States is estimated that only 10–15% of adult Caucasians react adversely to lactose, whereas 70% of adult Afro-Americans are lactose intolerance. The incidence of lactose intolerance in adult Asians is 95%. The beverage food industry could formulate a calcium- and magnesium-fortified beverage containing caprine caseinophosphopeptide to export to the Far East.

Example 8

Coated Nuts

Long shunned by dieters for their fat content, nuts have made a big-time dietary come back. Recent epidemiological studies suggest that frequent nut consumption may be protective against heart disease and other chronic diseases. As mentioned earlier, the level of fat in the diet influences magnesium absorption because fatty acids have a greater tendency to form soaps with calcium than magnesium (Van Dokkun et al. in Ann. Nutr. Metab. 27, 361–367 (1983)).

Recent research studies have shown that increased lipid proportion of the diet improves the digestive utilization of magnesium in clinical cases of malabsorption syndrome (Alférez et al. in J. Dairy Res. 68, 451–461 (2001)). Increased proportions of protein in the diet also favors magnesium absorption (Pallarés et al. in J. Agric. Food Chem. 44, 1816–1820 (1996)). Nuts are rich in fat, protein, and magnesium. The inventive antioxidant composition promotes a significant increase of magnesium absorption, which is reflected in the greater quantity of this mineral stored in femoral bone. Magnesium is associated with strong bones. People who crunch on nuts coated with the inventive antioxidant composition can lower the risk of bone fractures.

Although only exemplary embodiments of the invention are specifically described above, it will be appreciated that modifications and variations of these examples are possible without departing from the spirit and intended scope of the invention.

The invention claimed is:

1. An antioxidant composition comprising: 1) a polycationic chitosan casein phosphopeptide complex and 2) at least one oil rich in Omega-3 or an oil soluble active operable to inhibit oxidation, the at least one oil is selected from the group consisting of vegetable oils and animal oils; and the at least one oil soluble active is selected from the group consisting of vitamins, nutraceuticals, pharmaceuticals and combinations thereof.

2. The composition of claim 1 wherein the polycationic chitosan casein phosphopeptide is immiscible in oil.

3. The composition of claim 2, further comprising at least one sulfated polysaccharide wherein the sulfated polysaccharide is selected from the group consisting of iota-carrageenan, kappa-carrageenan, lambda-carrageenan, chondroitin, heparin, dextran, and cyclodextrins, and combinations thereof.

4. The composition of claim 1 wherein the polycationic chitosan casein phosphopeptide is a polycationic chitosan caprine case phosphopeptide.

5. The composition of claim 4, further comprising a medium-chain triglyceride wherein the medium-chain triglyceride is selected from the group consisting of: caproic (C:6.0), caprylic (C:8.0), and capric (C:10.0) triglycerides, and any combinations thereof.

6. The composition of claim 1, further comprising at least one non-reducing sugar or sugar polyol.

7. The composition of claim 1, wherein the casein phosphopeptide is selected from the group consisting of alpha-casein, beta-casein, kappa-casein, fragments thereof, and any combinations thereof.

8. The composition of claim 1, further comprising at least one ingredient selected from the group consisting of alpha, beta, gamma or delta tocopherols, alpha, beta, gamma or delta tocotrienols, tocopherols, tocotrienols, beta-carotene phospholipids, chitosan and combinations thereof.

9. The composition of claim 1, further comprising at least one phospholipid selected from the group consisting of egg yolk phospholipids, soybean phospholipids, and combinations thereof.

10. The composition of claim 1, further comprising at least one ingredient selected from the group consisting of pH modifiers, chelating agents, polyphenols, modified starches, glycerides, fruit concentrate sweeteners, cocoa powder, and sucralose.

11. The composition of claim 10, wherein the pH modifiers are selected from the group consisting of citric acid, ascorbic acid, gluconic acid, and combinations thereof.

12. The composition of claim 10, wherein the chelating agents comprise citric acid.

13. The composition of claim 10, wherein the polyphenols are derived from the fruit of *Solanum melongena*.

14. The composition of claim 1, wherein the emulsion is selected from the group consisting of water-in-oil microemulsion, water-in-oil nanoemulsion, oil-in-water microemulsion, and oil-in-water nanoemulsion.

15. The composition of claim 1, wherein the casein phosphopeptide comprises a trypsin-digested casein.

16. The composition of claim 15, wherein the trypsin-digested casein is selected from the group consisting of caprine casein characterized by a content of alpha.sub.s2.-casein greater than 15 percent and beta-casein greater than 15 percent of the total casein.

17. The composition of claim 1, wherein the vegetable oil is selected from the group consisting of rice bran oil, flax oil, chia oil, hemp oil, castor oil, soybean oil, lesquerella oil, dehydrated castor oil, oil rich in Omega-3 and vegetable oils containing conjugated linoleic acid.

18. The composition of claim 1, wherein the animal oil is selected from the group consisting of fish oil, egg oil, poultry oil, beef oils rich in Omega-3 and animal oils containing conjugated linoleic acid.

19. An antioxidant composition comprising: 1) a polycationic chitosan casein fragment complex immiscible in oil, wherein said casein fragrament is a phosphopeptide, and 2) at least one oil or an oil soluble active operable to inhibit oxidation, wherein said at least one oil is selected from the group consisting of vegetable oils comprising rice bran oil, flax oil, chia oil, hemp oil, castor oil, soybean oil, lesquerella oil, dehydrated castor oil, oil rich in Omega-3, or vegetable oils containing conjugated linoleic acid, and animal oils comprising fish oil, egg oil, poultry oil, and beef oils rich in Omega-3, or animal oils containing conjugated linoleic acid; wherein said oil-soluble actives comprise vitamins, nutraceuticals, pharmaceuticals, flavors, or combinations thereof.

20. The composition of claim 19, wherein the casein fragment is characterized by a content of alpha.sub.s2.-casein greater than 15 percent of total casein and medium-chain triglycerides.

21. The composition of claim 19, wherein the caseinophosphopeptide comprises a caprine caseinophosphopeptide.

22. The composition of claim 19, further comprising at least one ingredient selected from the group consisting of alpha, beta, gamma or delta tocopherols, alpha, beta, gamma or delta tocotrienols, tocopherols, tocotrienols, beta-carotene, phospholipids, chitosan and combinations thereof.

23. The composition of claim 19, further comprising at least one phospholipid selected from the group consisting of egg yolk phospholipids, soybean phospholipids, and combinations thereof.

24. The composition of claim 19, further comprising at least one ingredient selected from the group consisting of pH modifiers, chelating agents, polyphenols, modified starches, glycerides, fruit concentrate sweeteners, cocoa powder, sucralose, and oil-soluble flavors, vitamins, nutraceutical actives, and pharmaceutical actives.

25. The composition of claim 24, wherein the fruit concentrate sweetener comprises a blend of hydrolyzed starch having a dextrose equivalent of up to approximately 25; fruit juice or fruit syrup concentrate of at least approximately 40% soluble solids; and approximately 0% insoluble solids, wherein the starch, juice or concentrate and solids form a liquor having a dry weight composition of approximately 40 to approximately 65% complex carbohydrates, approximately 35 to approximately 55% simple sugars from the fruit juice or fruit syrup concentrate, and approximately 0 to approximately 5% nutritional components occurring naturally in the fruit juice or fruit syrup concentrate.

26. The composition of claim 19, further comprising a polyphenol selected from the group consisting of *Solanum melongena* polyphenols.

27. The composition of claim 19, further comprising non-reducing sugars and sugar polyols.

28. The composition of claim 19, further comprising pH modifiers wherein the acidic environment ranges from pH 2.0 to 5.7.

29. The composition of claim 19, further comprising sulfated polysaccharides selected from the group consisting of carrageenans, chondroitin, heparin, dextran, cyclodextrins and combinations thereof.

30. The composition of claim 19, wherein the glyceride is selected from the group consisting of enzymatically modified oils, fats, and fatty acids of mono-, di-, and tri-glycerides; lipolyzed modified oils, fats, and fatty acids of mono-, di-, and tri-glycerides; and combinations thereof.

31. The composition of claim 19, wherein the polycationic casein fragment is a polycationic caprine casein fragment.

32. An product comprising 1) at least one polycationic chitosan casein phosphopeptide complex, wherein the polycationic chitosan casein phosphopeptide complex imparts at least one function selected from the group consisting of inhibiting oxidation of oil-in-water or water-in-oil emulsions, preventing bone mineral loss in a mammal, and preventing hypercholesterolemia in a mammal and 2) at least one oil or an oil soluble active operable to inhibit oxidation selected from the group consisting of vegetable oils comprising rice bran oil, flax oil, chia oil, hemp oil, castor oil, soybean oil, lesquerella oil, dehydrated castor oil, oil rich in Omega-3, or vegetable oils containing conjugated linoleic acid, and animal oils comprising fish oil, egg oil, poultry oil, and beef oils rich in Omega-3, or animal oils containing conjugated linoleic acid; wherein said oil-soluble actives comprise vitamins, nutraceuticals, pharmaceuticals, flavors, or combinations thereof.

33. The product of claim 32, wherein the product is selected from the group consisting of cocoa products, hypercholesterolemia preventatives, bone mineral loss preventatives, Omega-3-rich oil products, protein rich products having reduced protein settling and sedimentation, and transparent beverages.

34. The composition of claim 32, wherein the polycationic casein phosphopeptide is a caseinophosphopeptide-chitosan complex immiscible in oil.

35. The composition of claim 32, wherein the polycationic casein phosphopeptide is a polycationic caprine casein phosphopeptide.

\* \* \* \* \*

UNITED STATES PATENT AND TRADEMARK OFFICE
CERTIFICATE OF CORRECTION

PATENT NO. : 7,118,688 B2
APPLICATION NO. : 10/784842
DATED : October 10, 2006
INVENTOR(S) : Adela Mora-Gutierrez et al.

It is certified that error appears in the above-identified patent and that said Letters Patent is hereby corrected as shown below:

Column 5 - Line 44:
   Please delete " C" and insert -- C° --

Column 9 - Line 66:
   Please delete "OW" and insert -- O/W --

Column 10 - Line 10:
   Please delete "deserts" and insert -- desserts --

Column 11 - Line 48:
   Please delete "v/v" and insert -- w/v --

Column 14 - Line 59:
   Please delete "caseinophos-phopeptide" and insert -- caseinophosphopeptide --

Column 14 - Line 66:
   Please delete the second instance of "caprine"

Column 15 - Line 33:
   Please delete "powered" and insert -- powdered --

Column 15 - Line 50:
   Please delete "caseino-phosphopeptide" and insert -- caseinophosphopeptide --

Column 15 - Line 54:
   Please delete "powered" and insert -- powdered --

Column 16 - Line 55 to line 56:
   Please delete "powered" and insert -- powdered --

Column 17 - Line 30:
   Please delete "powered" and insert -- powdered --

Column 18 - Line 56:
   Please delete "caseinophospho-peptide" and insert -- caseinophosphopeptide --

Column 21 - Line 5:
   Please delete "States is" and insert -- States, it is --

Column 21 - Line 8:
   Please delete "intolerance" and insert -- intolerant --

UNITED STATES PATENT AND TRADEMARK OFFICE
CERTIFICATE OF CORRECTION

PATENT NO. : 7,118,688 B2
APPLICATION NO. : 10/784842
DATED : October 10, 2006
INVENTOR(S) : Adela Mora-Gutierrez et al.

It is certified that error appears in the above-identified patent and that said Letters Patent is hereby corrected as shown below:

Column 21 - Claim 4 - Line 3:
    Please delete "case" and insert -- casein --

Column 22 - Claim 8 - Line 4:
    Please delete "beta-carotene phospholipids" and insert -- beta-carotene, phospholipids --

Column 24- Claim 32 - Line 1:
    Please delete "comprising 1)" and insert -- comprising: 1) --

Signed and Sealed this

Seventeenth Day of July, 2007

JON W. DUDAS
*Director of the United States Patent and Trademark Office*